United States Patent [19]

Halley

[11] Patent Number: 4,481,296

[45] Date of Patent: Nov. 6, 1984

[54] COLOR INDICATOR SYSTEM FOR PH MEASUREMENT

[75] Inventor: James L. Halley, Mableton, Ga.

[73] Assignee: Great Lakes Chemical Corporation, West Lafayette, Ind.

[21] Appl. No.: 466,432

[22] Filed: Feb. 15, 1983

[51] Int. Cl.³ .............................................. G01N 21/80
[52] U.S. Cl. .................................... 436/163; 436/175; 549/33
[58] Field of Search ................... 436/163, 175; 549/33

[56] References Cited

U.S. PATENT DOCUMENTS 4,382,122  5/1983  Mezei et al. ..................... 549/33 X

FOREIGN PATENT DOCUMENTS 783685  11/1980  Japan .................................... 436/163

OTHER PUBLICATIONS

Vogel, *Textbook of Quantitative Inorganic Analysis*, 4th Edition, pp. 240–243.
Method 405, *Standard Methods for the Examination of Water and Waste Water*, 15th Edition, p. 261.

*Primary Examiner*—Arnold Turk
*Attorney, Agent, or Firm*—Kirkland & Ellis

[57] ABSTRACT

A composition comprising phenol red, phenol, and deionized water and preferably sodium hydroxide and citric acid and a method for measuring pH wherein such composition is added to a water sample.

11 Claims, No Drawings

COLOR INDICATOR SYSTEM FOR PH MEASUREMENT

BACKGROUND OF THE INVENTION

1. Field of the Invention

This invention relates to a stabilized phenol red indicator composition capable of providing visual pH measurements of water in the presence or absence of a halogen.

2. Description of Prior Art

The acid-base indicator phenol red undergoes a color change in the pH range of 6.4 to 8.0 and is commonly used to measure the pH of swimming pool water. See Vogel, *Textbook of Quantitive Inorganic Analysis* 4th Ed., 240–43. However, in the presence of bromine ($Br_2$), hypobromous acid or the hypobromite ion, especially higher levels, phenol red undergoes bromination (as shown in reaction I)

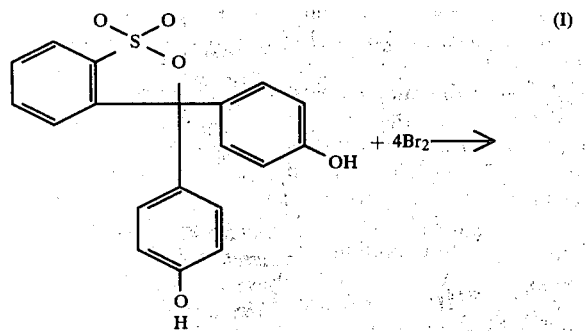

Phenol Red

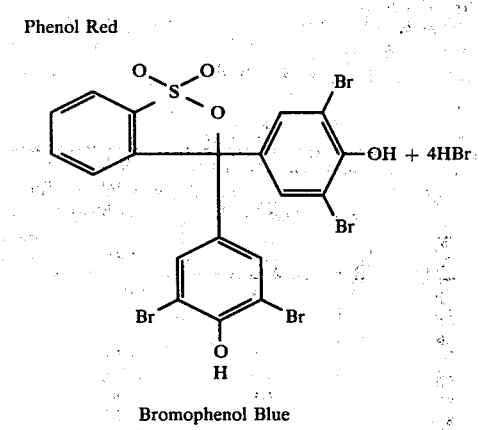

Bromophenol Blue to form bromophenol blue, an acid-base indicator which undergoes color change in the pH range of 3.2–4.6. In fact, the reaction of bromine with phenol red is employed as a method to determine bromide ion in water. See Method 405, *Standard Methods for the Examination of Water and Wastewater*, 15th Ed., p. 261. The complete conversion of phenol red to bromophenol blue makes measurement of the pH of a swimming pool impossible, while incomplete conversion of phenol red to bromophenol blue sharply reduces the usefulness of phenol red since pH measurements are erratic and inaccurate.

It is known to those practicing the art that phenol red indicator solutions are marketed containing sodium thiosulfate which is intended to function as a free halogen scavenger. This intended solution to the problem of the bromination conversion of phenol red to bromophenol blue is unsatisfactory in practice for the following reasons:

(1) incomplete and inconsistent protection against the bromination conversion of phenol red to bromophenol blue in the presence of free bromine, (2) inability to accurately measure pH in the presence of high free bromine residuals (higher than 15 ppm $Br_2$), (3) formation of reaction products that affect the pH measurement, even at lower free bromine residuals.

Improper treatment of pool water due to an inaccurate pH reading may cause damage to the pool and equipment or reduce the effectiveness of the water sanitizer. If the pH falls below the recommended range, damage to the pool and equipment may result. Concrete etching, vinyl liner damage, and corrosion of metal parts are possible in low pH water. If pH rises above the recommended range, the effectiveness of the water sanitizer is reduced because of its conversion to the less effective hypohalite ion. Both high and low pH cause bather discomfort.

Although many compounds react with halogen in the aqueous system of concern, a compound of practical utility must permit the formulation of an indicator solution with the following characteristics:

A. Complete solubility in water and freedom from color, both as formulated and after reaction with bromine, B. The ability, when used, to reduce the free bromine residual rapidly and completely without appreciable alteration of the system's pH, C. Long-term shelf life stability, D. The ability, when used, to indicate pH accurately as compared, for example, to the results obtained with a well-calibrated pH meter, E. The ability, when used, to adapt directly for use with a commercially available pH test block comparator, such as that used with the Taylor Chemicals, Inc. Test Kit No. 2100.

Accordingly, it is the principal object of the present invention to provide a simple and inexpensive composition which, in the presence of water containing or not containing a halogen, will provide an accurate, visual pH measurement.

It is a further object of the present invention to provide a pH-measuring composition having a shelf stability of at least one year.

SUMMARY OF INVENTION

In accordance with the subject invention, the foregoing objects, advantages, and features have been achieved with a stabilized color indicator composition comprising phenol red, phenol and deionized water in effective amounts. Preferably, sodium hydroxide and citric acid are also present.

DETAILED DESCRIPTION OF THE PREFERRED EMBODIMENTS

In accordance with the subject invention, it has been found that an improved composition capable of measuring the pH of water in the presence or absence of a halogen may be obtained by providing in combination:

phenol red, preferably in an amount greater than about 0 to about 2 weight percent of the composition;

phenol, preferably greater than about 0 to about 10 weight percent;

sodium hydroxide, preferably about 0 to 1 weight percent;

citric acid, preferably about 0 to about 1 weight percent; and deionized water, preferably about 88 to 99 weight percent.

The color developed by the addition of this indicator solution to a water sample is compared against a set of permanent color standards (color blocks or color solutions) in order to ascertain the pH of the water sample. The color developed is unaffected by halogen residuals up to at least about 80 ppm of the halogen in the water sample. Examples of suitable sources for water samples are swimming pool water, spa and hot tub water, drinking water, recirculating cooling tower water, once-through cooling tower water, irrigation water, oil field injection water, and treated waste water.

In the composition of this invention, phenol absorbs halogen in the water sample, thereby stabilizing the phenol red against halogenation. The phenol absorbs bromine, for example, to prevent the bromination reaction shown in reaction I. Citric acid acts to tie up iron and copper ions in the water sample. Such ions, in the absence of citric acid, will react with the phenol red, adversely affecting its operation as an acid-base indicator. Sodium hydroxide is preferentially employed to adjust the pH of the composition.

An exemplary method for measuring the pH of a water sample in accordance with this invention is given in the following examples.

EXAMPLE I

An indicator solution was prepared by dissolving 1.20 grams of Hellige Phenol Red W.S. No. R1518P and 12.50 grams of phenol (Mallincrodt Reagent Grade) in 200 ml of deionized water in a 500 ml volumetric flask. After the components were dissolved, the flask was filled to 500 ml with deionized water and allowed to stand for 24 hours. The pH of the solution was 7.2. The solution was transferred to a 1 liter beaker and sodium hydroxide (50% solution—Baker Reagent Grade) was added with stirring from a microburet until a pH of 8.5 was maintained for five minutes. A total of 0.215 ml of 50% sodium hydroxide (Baker Reagent Grade) (0.328 grams) was added during this step. With stirring, citric acid (anhydrous—Fisher Reagent Grade) was slowly added.

The solution was used to measure the pH of a wide variety of swimming pool and spa waters. The results are shown in Table I. When the free bromine residual exceeds about 15.0 ppm, the pH cannot be determined using the standard indicator. The stabilized phenol red gives good agreement with the pH as determined by the pH meter up to a free bromine residual of 80 ppm. At 118 ppm, the bromophenol blue conversion occurs in the stabilized indicator. In addition, good agreement between the pH values measured by the pH meter and by the stabilized phenol red indicator are obtained when the free bromine residual is at or near zero.

EXAMPLE II

An indicator solution was prepared by dissolving 0.20 grams of Hellige Phenol Red W.S. No. R1518P and 25.00 grams of phenol (Mallincrodt Reagent Grade) in 500 ml of deionized water in a 1000 ml volumetric flask. After the components were dissolved, the flask was filled to the 1000 ml mark with deoionized water. After one hour, the solution was transferred to a 2 liter breaker. The pH of the solution was 4.28. With stirring, sodium hydroxide (50% solution Baker Reagent Grade) was added from a microburet until a pH of 8.5 was maintained for five minutes. A total of 0.670 ml of 50% sodium hydroxide (Baker Reagent Grade) (1.022 grams) was added during this step. With stirring, citric acid (anhydrous Fisher Reagent Grade) was slowly added to the solution until the pH reached 7.5. A total of 0.33 grams of citric acid was added.

The solution was used to measure the pH of a wide variety of swimming pool and spa waters. The results are shown in Table II. When the free bromine residual is above 10 ppm, the pH cannot be determined using the standard indicator. The stabilized phenol red gives good agreement with the pH as determined by the pH meter. A limiting value for the bromine residuals was not reached in this example. No difficulties were noted at free bromine residuals of about 47 ppm.

EXAMPLE III

The stability (shelf-life) of the indicator formulation was studied over a period of one year. Samples of water from an active swimming pool were obtained. The bromine residual was adjusted to 35 ppm $Br_2$ and the pH of one portion of the sample adjusted to 7.0 (as measured by a pH meter) by the addition of hydrochloric acid, and the pH of a second portion to 8.0 (as measured by a pH meter) by the addition of sodium hydroxide. The pH of each solution was determined using a color block and the phenol stabilized phenol red indicator. The bromine residual of the test solution was also determined after the addition of the stabilized phenol red. The results are shown in Table III. A small bromine residual appears at about 300 days indicating that the degree of protection against high bromine residuals is decreasing. However, no loss of precision of pH measurement is observed. Excellent results are obtained for a period of at least one year.

TABLE I

Evaluation of Stabilized Phenol Red Indicator for use with the Taylor Chemicals, Inc. 2100 Test Kit

| Test | Watery Source | Free $Br_2$ (ppm) | Combined $Br_2$ (ppm) | Meter | 2100[2] | Stabilized Phenol Red |
|---|---|---|---|---|---|---|
| 1 | Spa | 8.6 | 1.8 | 7.80 | 8.0 | 7.8 |
| 2 | Spa | 11.3 | 0.5 | 7.70 | 8.2 | 7.8 |
| 3 | Spa | 14.4 | 0.9 | 7.15 | 7.4 | 7.6 |
| 4 | Spa | 17.6 | 0.9 | 7.70 | BPBC[1] | 7.8 |
| 5 | Spa | 21.6 | 4.3 | 7.70 | BPBC | 7.8 |
| 6 | Spa | 43.7 | 0.9 | 7.40 | BPBC | 7.7 |
| 7 | Spa | 50.0 | 4.0 | 7.78 | BPBC | 7.9 |
| 8 | Spa | 18.0 | 2.6 | 7.83 | 7.8 | 7.8 |
| 9 | Spa | 35.0 | 4.0 | 7.78 | BPBC | 7.8 |
| 10 | Spa | 80.0 | 86.0 | 8.12 | BPBC | 8.2 |
| 11 | Spa | 118.0 | 11.0 | 7.62 | BPBC | BPBC |
| 12 | Pool | 0.0 | 0.6 | 7.81 | 7.8 | 7.8 |
| 13 | Pool | 0.6 | 0.4 | 7.28 | 7.4 | 7.4 |
| 14 | Pool | 4.0 | 0.5 | 7.68 | 7.8 | 7.6 |
| 15 | Pool | 14.4 | 0.5 | 7.70 | 7.6 | 7.8 |

[1]BPBC - Bromophenol blue conversion
[2]Standard Phenol Red Indicator

TABLE II

Evaluation of Stabilized Phenol Red Indicator for Determining pH with Taylor Chemicals, Inc. 1003J Professional Test Kit

| Test | Water Source | Free $Br_2$ (ppm) | Combined $Br_2$ (ppm) | Meter | 1003J[2] | Stabilized Phenol Red |
|---|---|---|---|---|---|---|
| 1 | Spa | 0.8 | 1.6 | 7.45 | 7.5 | 7.4 |

TABLE II-continued

Evaluation of Stabilized Phenol Red Indicator for
Determining pH with Taylor Chemicals, Inc.
1003J Professional Test Kit

| Test | Water Source | Free Br$_2$ (ppm) | Combined Br$_2$ (ppm) | pH Measured by | | |
|---|---|---|---|---|---|---|
| | | | | Meter | 1003J[2] | Stabilized Phenol Red |
| 2 | Spa | 7.1 | 5.4 | 7.60 | 7.7 | 7.6 |
| 3 | Spa | 8.6 | 1.8 | 7.80 | 7.9 | 7.8 |
| 4 | Spa | 9.9 | 1.4 | 7.60 | BPBC[1] | 7.5 |
| 5 | Spa | 11.0 | 4.6 | 7.75 | 8.0 | 7.7 |
| 6 | Spa | 11.3 | 0.5 | 7.70 | 7.8 | 7.8 |
| 7 | Spa | 11.6 | 3.8 | 7.85 | BPBC | 7.8 |
| 8 | Spa | 13.5 | 2.7 | 6.85 | 6.9 | 6.9 |
| 9 | Spa | 14.0 | 3.2 | 7.75 | 8.0 | 7.7 |
| 10 | Spa | 14.4 | 0.9 | 7.15 | 7.3 | 7.3 |
| 11 | Spa | 17.6 | 0.9 | 7.70 | BPBC | 7.8 |
| 12 | Spa | 18.0 | 4.4 | 7.80 | BPBC | 7.8 |
| 13 | Spa | 20.7 | 7.2 | 7.70 | BPBC | 7.7 |
| 14 | Spa | 21.2 | 1.2 | 7.65 | BPBC | 7.6 |
| 15 | Spa | 21.6 | 4.2 | 7.70 | 7.7 | 7.7 |
| 16 | Spa | 31.2 | 2.2 | 7.05 | 7.2 | 7.1 |
| 17 | Spa | 31.9 | 2.8 | 7.85 | BPBC | 7.9 |
| 18 | Spa | 34.0 | 2.4 | 7.50 | BPBC | 7.5 |
| 19 | Spa | 38.0 | 2.0 | 7.50 | BPBC | 7.6 |
| 20 | Spa | 43.7 | 0.9 | 7.40 | BPBC | 7.5 |
| 21 | Spa | 46.8 | 5.0 | 7.85 | BPBC | 7.8 |
| 22 | Pool | 2.6 | 4.8 | 7.45 | 7.5 | 7.5 |
| 23 | Pool | 4.4 | 0.6 | 7.35 | 7.4 | 7.4 |
| 24 | Pool | 4.4 | 2.0 | 7.60 | 7.6 | 7.6 |
| 25 | Pool | 6.8 | 1.6 | 7.65 | 7.6 | 7.6 |
| 26 | Pool | 7.4 | 1.4 | 7.60 | 7.6 | 7.6 |
| 27 | Pool | 7.6 | 1.8 | 8.00 | 8.0 | 7.9 |
| 28 | Pool | 11.3 | 2.3 | 7.60 | 7.6 | 7.6 |
| 29 | Pool | 14.4 | 0.5 | 7.70 | 7.8 | 7.8 |
| 30 | Pool | 18.0 | 1.8 | 7.85 | BPBC | 7.8 |
| 31 | Pool | 19.4 | 2.6 | 7.65 | 7.8 | 7.6 |
| 32 | Pool | 25.0 | 1.4 | 7.35 | 7.7 | 7.5 |
| 33 | Pool | 34.4 | 1.6 | 7.60 | BPBC | 7.6 |

[1]BPBC - Bromophenol blue conversion
[2]Standard phenol red indicator

TABLE III

Stability Study

| Elapsed Time (days) | Final Free Br$_2$ (ppm) | pH Measured by | | Final Free Br$_2$ (ppm) | pH Measured by | |
|---|---|---|---|---|---|---|
| | | Meter | Stabilized Phenol Red | | Meter | Stabilized Phenol Red |
| 0 | 0 | 7 | 7 | 0 | 8 | 8 |
| 2 | 0 | 7 | 7 | 0 | 8 | 8 |
| 11 | 0 | 7 | 7 | 0 | 8 | 8 |
| 24 | 0 | 7 | 7 | 0 | 8 | 8 |
| 45 | 0 | 7 | 7 | 0 | 8 | 8 |
| 68 | 0 | 7 | 7 | 0 | 8 | 8 |
| 169 | 0 | 7 | 7 | 0 | 8 | 8 |
| 182 | 0 | 7 | 7 | 0 | 8 | 8 |
| 215 | 0 | 7 | 7 | 0 | 8 | 8 |
| 248 | 0 | 7 | 7 | 0 | 8 | 8 |
| 285 | 0 | 7 | 7 | 0 | 8 | 8 |
| 319 | 0.5 | 7 | 7 | 0.5 | 8 | 8 |
| 355 | 1.0 | 7 | 7 | 1.0 | 8 | 8 |
| 367 | 1.0 | 7 | 7 | 1.0 | 8 | 8 |

I claim:

1. A stabilized color indicator composition capable of measuring pH in the presence of halogens comprising pheno red, phenol in an amount effective to bind halogens present in a sample to be anaylzed and deionized water.

2. A composition, as claimed in claim 1, which comprises:
   from greater than about 0 to about 2 weight percent phenol red;
   from greater than about 0 to about 10 weight percent phenol; and
   from about 88 to about 99 weight percent deionized water.

3. A composition, as claimed in claim 1, which additionally comprises citric acid.

4. A composition, as claimed in claim 1, which additionally comprises sodium hydroxide.

5. A composition, as claimed in claim 1, which comprises:
   from greater than about 0 to about 2 weight percent phenol red;
   from greater than about 0 to about 10 weight percent phenol;
   from about 0 to about 1 weight percent sodium hydroxide;
   from greater than about 0 to about 1 weight percent citric acid; and
   from about 88 to about 99 weight percent deionized water.

6. A method of measuring pH of an aqueous system comprising the steps of:
   withdrawing a representative sample from the aqueous system;
   adding to the representative sample a composition comprising phenol red, phenol in an amount effective to bind halogens present in the sample and deionized water thereby forming an analysis sample; and
   observing a color change or lack thereof in the representative sample.

7. A method, as claimed in claim 6, wherein the composition comprises:
   from greater than about 0 to about 2 weight percent phenol red;
   from greater than about 0 to about 10 weight percent phenol; and
   from about 88 to about 99 weight percent deionized water.

8. A method, as claimed in claim 6, wherein the composition additionally comprises citric acid.

9. A method, as claimed in claim 6, wherein the composition additionally comprises sodium hydroxide.

10. A method, as claimed in claim 6, wherein the composition comprises:
    from greater than about 0 to about 2 weight percent phenol red;
    from greater than about 0 to about 10 weight percent phenol;
    from about 0 to about 1 weight percent sodium hydroxide;
    from greater than about 0 to about 1 weight percent citric acid; and
    from about 88 to about 99 weight percent deionized water.

11. A method, as claimed in claim 6, wherein the color change is detected by comparing the analysis sample against a color standard.

* * * * *